(12) United States Patent
Balashanmugam et al.

(10) Patent No.: US 10,844,298 B2
(45) Date of Patent: Nov. 24, 2020

(54) PREDICTING SOLVENT POWER OF LIGHT OILS

(71) Applicant: BP Corporation North America Inc., Houston, TX (US)

(72) Inventors: Soban Balashanmugam, Surrey (GB); Ronald Fisher, San Antonio, TX (US); Rosa Rueda-Velásquez, Naperville, IL (US); Devin Halliday, Chicago, IL (US)

(73) Assignee: BP Corporation North America Inc., Houston, TX (US)

( * ) Notice: Subject to any disclaimer, the term of this patent is extended or adjusted under 35 U.S.C. 154(b) by 296 days.

(21) Appl. No.: 15/239,019

(22) Filed: Aug. 17, 2016

(65) Prior Publication Data

US 2017/0058216 A1    Mar. 2, 2017

Related U.S. Application Data

(60) Provisional application No. 62/212,781, filed on Sep. 1, 2015.

(51) Int. Cl.
| | | |
|---|---|---|
| *C10G 75/00* | (2006.01) | |
| *G01N 33/28* | (2006.01) | |
| *G01N 31/16* | (2006.01) | |

(52) U.S. Cl.
CPC ............ *C10G 75/00* (2013.01); *G01N 31/16* (2013.01); *G01N 33/2823* (2013.01); *C10G 2300/206* (2013.01); *C10G 2300/802* (2013.01)

(58) Field of Classification Search
CPC ........... G01N 33/2829; G01N 33/2835; G01N 33/2823; G01N 33/241; G01N 31/16; G01N 31/02; E21B 49/087; E21B 2049/085

See application file for complete search history.

(56) References Cited

U.S. PATENT DOCUMENTS 5,871,634 A    2/1999 Wiehe et al.
2004/0121472 A1    6/2004 Nemana et al.

FOREIGN PATENT DOCUMENTS

WO    WO 2015/087049    6/2015

OTHER PUBLICATIONS

Andersen, Simon Ivar. "Flocculation onset titration of petroleum asphaltenes." Energy & Fuels (1999) 13 315-322. (Year: 1999).*
The UTS Website, obtained by the examiner on Sep. 11, 2018 from an archive made on Aug. 10, 2013 <http://web.archive.org/web/20060715000000*/https://www.uts.conn/ResourceCenter/ProductTraining/TK5AdvancedTraining.pdf>. (Year: 2013).*
Alomair, Osmah et al. "Heavy crude oil viscosity reduction and the impact of asphaltene precipitation." Energy and Fuels (2013) 27 7267-7276. (Year: 2013).*

* cited by examiner

*Primary Examiner* — Christopher Adam Hixson
(74) *Attorney, Agent, or Firm* — McDonnell Boehnen Hulbert & Berghoff LLP

(57) ABSTRACT

A method for recalculating the solvent power of a light oil, $SP_{(LO\ recalculated)}$, is provided. The method comprises:

titrating the light oil against a reference oil, optionally in the presence of a titrant, to determine a volume fraction of the light oil at the onset of asphaltene precipitation, $V_{(onset\ fraction\ LO)}$, a volume fraction of the reference oil at the onset of asphaltene precipitation, $V_{(onset\ fraction\ RO)}$, and, where a titrant is present, a volume fraction of the titrant at the onset of asphaltene precipitation, $V_{(onset\ fraction\ T)}$, and determining the recalculated solvent power of the light oil, $SP_{(LO\ recalculated)}$, according to the following formula:

$$SP_{(LO\ recalculated)} = \frac{\left( CSP_{(RO)} - SP_{(RO)} * V_{(onset\ fraction\ RO)} - x * SP_{(T)} * V_{(onset\ fraction\ T)} \right)}{V_{(onset\ fraction\ LO)}}$$

wherein: $CSP_{(RO)}$ is the critical solvent power of the reference oil,
$SP_{(RO)}$ is the solvent power of the reference oil,
$SP_{(T)}$ is the solvent power of the titrant, and
x is 1 where a titrant is present, and otherwise is 0.

The recalculated solvent power may be used in methods for preventing asphaltene precipitation during processing of crude oils in a refinery.

18 Claims, 4 Drawing Sheets

PREDICTING SOLVENT POWER OF LIGHT OILS

FIELD OF THE INVENTION

The present invention relates to methods for predicting the solvent power of a light oil. In particular, the present invention relates to methods for predicting the solvent power of a light crude oil.

BACKGROUND OF THE INVENTION

It is often desirable to blend crude oils from different sources before processing in a refinery. There are a number of reasons for combining crude oils in this way.

For instance, there may be period where a particular type of crude oil is in plentiful supply, and thereby relatively low cost. However, certain types of crude oil may have properties which make them less attractive for refining or for further sale. In these scenarios, it is desirable to combine a crude oil having one set of properties with a crude oil having another set of properties, so that the resulting blended crude provides properties which are preferred for the market. In many cases, it is desirable for a light crude oil to be added to a heavy crude oil.

Heavy crude oils typically contain asphaltenes. Asphaltenes are organic heterocyclic macro-molecules that usually represent the heaviest compounds in crude oil. Asphaltenes are defined as a solubility class and, whilst they are typically soluble in aromatic solvents such as toluene, they are insoluble in paraffinic solvents such as n-heptane.

Under normal refinery conditions, the asphaltenes in a heavy crude oil are generally stable and remain in solution. However, when a light crude oil—which typically contains a high proportion of paraffinic components—is added to a heavy crude oil, the asphaltenes may precipitate. As the precipitate begins to adhere to metal surfaces in the refinery, fouling occurs.

Fouling in process equipment can result in plugging of flow lines and loss of heat transfer efficiency due to poorer heat transfer through the foulant layer. Fouling may occur in any refinery process equipment that comes in contact with the blended crude oil. Such process equipment includes tanks, pipes, heat exchangers, fired heater (furnace) tubes, fractionators and reactors.

Accordingly, one of the biggest challenges faced by refineries that process crude oils is the ability to ensure that the asphaltenes in a blended crude oil are kept stable and in solution as the oil undergoes processing.

Useful properties for predicting whether asphaltene precipitation will occur include the critical solvent power (CSP) and the solvent power (SP) of a crude oil. When the solvent power falls below the critical solvent power, asphaltenes begin to precipitate from the crude oil. Increased asphaltene precipitation is observed as the solvent power falls further below the critical solvent power.

U.S. Pat. No. 5,871,634 describes a method for blending two or more petroleum streams, at least one of which contains asphaltenes. As part of the method, the insolubility number and the solubility blending number of each stream are determined. The method is purported to allow blending of the petroleum streams without precipitation of the asphaltenes from solution.

US 2004/0121472 describes a method for blending two hydrocarbon liquids. As part of the method, the solvent power of each liquid is determined from the characterisation K factor. Heptane and toluene are used as solvent power references, with heptane having a solvent power of 0 and toluene having a solvent power of 100. The two hydrocarbon liquids are then blended so that the solvent power of the blend is greater than the critical solvent power of the crude oil having the highest critical solvent power in the blend.

Although the characterisation K factor is a convenient and simplistic means for estimating solvent power, it does not always match with experimentally determined values. Accordingly, asphaltene precipitation may be observed on adding an amount of light crude oil to a heavy crude oil, though precipitation has not been predicted using the characterisation K factor. Similarly, in some instances a greater amount of light crude oil may be added to a heavy crude oil without the onset of asphaltene precipitation than predicted using the characterisation K factor.

Accordingly, there is a need for a method for accurately determining or predicting the solvent properties of a light crude oil, so that the light crude oil may be combined with a heavy crude oil in an amount which does not lead to asphaltene precipitation.

SUMMARY OF THE INVENTION

The present invention provides a method for recalculating the solvent power of a light oil, $SP_{(LO\ recalculated)}$, said method comprising:

titrating the light oil against a reference oil, optionally in the presence of a titrant, to determine a volume fraction of the light oil at the onset of asphaltene precipitation, $V_{(onset\ fraction\ LO)}$, a volume fraction of the reference oil at the onset of asphaltene precipitation, $V_{(onset\ fraction\ RO)}$, and, where a titrant is present, a volume fraction of the titrant at the onset of asphaltene precipitation, $V_{(onset\ fraction\ T)}$, and determining the recalculated solvent power of the light oil, $SP_{(LO\ recalculated)}$, according to the following formula:

$$SP_{(LO\ recalculated)} = \frac{\left(\begin{array}{c}CSP_{(RO)} - SP_{(RO)} * V_{(onset\ fraction\ RO)} - \\ x * SP_{(T)} * V_{(onset\ fraction\ T)}\end{array}\right)}{V_{(onset\ fraction\ LO)}}$$

wherein:

$CSP_{(RO)}$ is the critical solvent power of the reference oil, $SP_{(RO)}$ is the solvent power of the reference oil, $SP_{(T)}$ is the solvent power of the titrant, and x is 1 where a titrant is present, and otherwise is 0.

The present invention further provides a method for determining a relationship between the recalculated solvent power and the bulk properties of lights oils, said method comprising:

determining the recalculated solvent power for a plurality of light oils using a method disclosed herein, and determining a relationship between the recalculated solvent power and the bulk properties of the plurality of light oils.

Also provided is a method for predicting the recalculated solvent power of a light oil, said method comprising using a relationship determined according to a method disclosed herein to predict the recalculated solvent power of the light oil from its bulk properties.

Also provided is a method of reducing the precipitation of asphaltene from a blend of a light oil and a heavy oil in a refinery, said method comprising:

determining the recalculated solvent power of the light oil or predicting the recalculated solvent power of the light oil using a method disclosed herein;

calculating, based on the recalculated solvent power of the light oil, a maximum ratio of light oil that may be included in a blend of the light oil and the heavy oil without asphaltene precipitation occurring in the refinery; and feeding a blend of the light oil and the heavy oil having up to the maximum ratio of light oil to the refinery.

By measuring the solvent power of a light oil relative to a reference oil, and optionally a titrant, the solvent power of light oils may be predicted accurately. The accurate prediction of the solvent power of a light oil allows for improved oil blending operations in which the risk of asphaltene precipitation is minimized.

Moreover, the present invention enables the solvent power of a light oil to be predicted merely from its bulk properties. This can help inform decisions on crude oil purchase, as well as on blending and scheduling for a refinery, when a physical sample of the oil is not available for laboratory analysis.

DETAILED DESCRIPTION OF THE INVENTION

Figure 1:
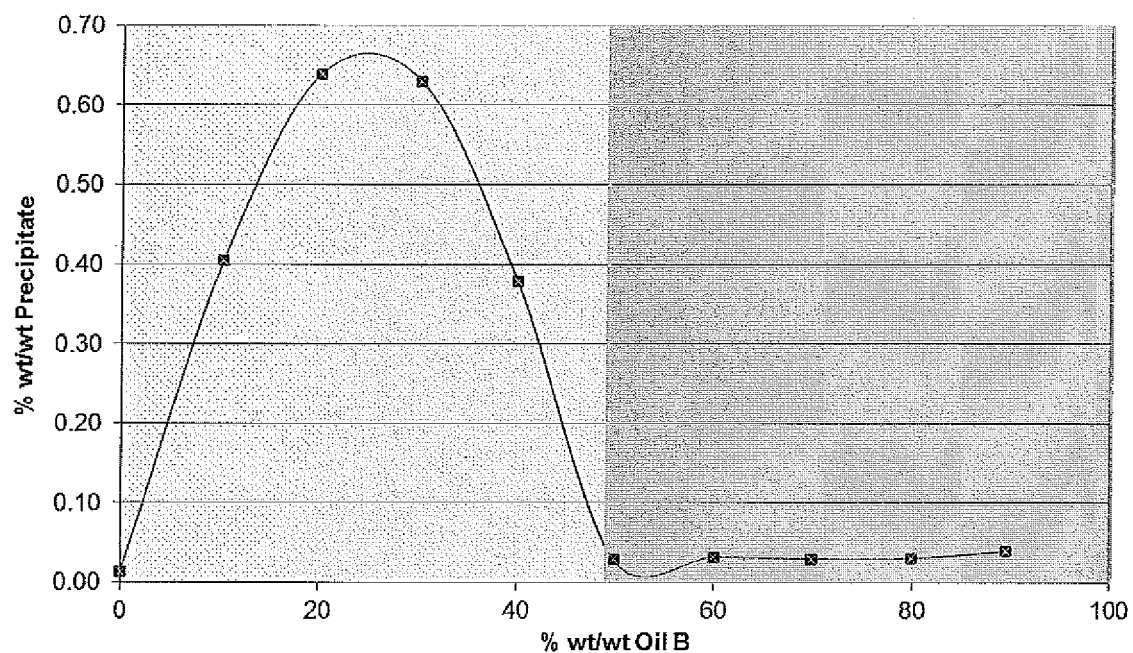
FIG. 1 is a graph showing the % by weight of precipitate that forms at different mixing ratios of a light crude oil, Oil A, with a heavy crude oil, Oil B.

Determining the Solvent Power and the Critical Solvent Power of the Reference Oil The formula for determining the recalculated solvent power of the light oil, $SP_{(LO\ recalculated)}$, derives from the following relationship:

$$CSP_{(LO+RO)} = SP_{(RO)} * V_{(onset\ fraction\ RO)} + SP_{(LO)} * V_{(onset\ fraction\ LO)}$$
$$+ x * SP_{(T)} * V_{(onset\ fraction\ T)}$$

where:
$CSP_{(LO+RO)}$ is the critical solvent power for a blend of the light oil and the reference oil.

For the purposes of the present invention, $CSP_{(LO+RO)}$ is assumed to be equal to the larger of the critical solvent power of the light oil, $CSP_{(LO)}$, and the critical solvent power of the reference oil, $CSP_{(RO)}$. Since a light oil will have a small or zero critical solvent power, $CSP_{(LO+RO)}$ is taken to be equal to $CSP_{(RO)}$.

Any known method may be used to determine the solvent power of the reference oil, $SP_{(RO)}$, and the solvent power of the titrant, $SP_{(T)}$. The solvent power of the titrant, $SP_{(T)}$, will generally be known in the art. The solvent power of the reference oil, $SP_{(RO)}$, (and the solvent power of the titrant, $SP_{(T)}$, if not known) may be calculated using the methodology described in US 2004/0121472 (Nemana, S. et al: Predictive Crude Oil Compatibility Model; incorporated herein by reference), according to which solvent power is estimated using the characterisation K factor.

The characterisation K factor, $K_{(RO)}$, is calculated according to the following formula:

$$K_{(RO)} = VABP_{(RO)}^{1/3} / SG_{(RO)}$$

where:
$VABP_{(RO)}$ is the volume average boiling point of the reference oil, in degrees Rankine, and $SG_{(RO)}$ is the standard specific gravity of the reference oil.

The volume average boiling point of the reference oil, $VABP_{(RO)}$, may be determined using known methods. In some instances, $VABP_{(RO)}$ may be determined from the yield profile of the reference oil.

The yield profile of the reference oil may be determined from physical distillation, for instance according to ASTM D 2892 or ASTM D 5236. The yield profile of the reference oil may alternatively be determined using GC and high temperature simulated distillation (HT-SIMDIS). Use of GC analysis allows the hydrocarbon composition of the oil to be determined for components boiling in the $C_{1-9}$ hydrocarbon range. GC analysis may be carried out according to standard test method IP 601. HT-SIMDIS analysis may be carried out according to standard test method IP 545.

The standard specific gravity of the reference oil, $SG_{(RO)}$, is the ratio of the density of the reference oil to that of water at 60° F. (i.e. 15.6° C.). $SG_{(RO)}$ may be determined using known methods. For instance, the density of the reference oil may be measured experimentally according to ASTM D 4052 or ASTM D 5002. The solvent power of the reference oil, $SP_{(RO)}$, may be determined from the characterisation K factor using linear interpolation. For instance, $SP_{(RO)}$ may be determined from $K_{(RO)}$ based on the relationship between the characterisation K factor and the solubility parameter of heptane and toluene. The characterisation K factor and the solubility parameter of heptane and toluene are known in the art.

The critical solvent power of the reference oil, $CSP_{(RO)}$, may be determined by titrating the reference oil against a precipitant. In some instances, $CSP_{(RO)}$ may be determined according to the following formula:

$$CSP_{(RO)} = V_{(onset\ fraction\ RO(P))} * SP_{(RO)} / 100$$

where:
$V_{(onset\ fraction\ RO(P))}$ is the volume fraction of the reference oil at the onset of asphaltene precipitation with a precipitant; and $SP_{(RO)}$ is the solvent power of the reference oil, which may be determined as described above, e.g. based on the characterisation K factor.

The precipitant that is used for determining $CSP_{(RO)}$ preferably has a negligible solvent power, such as a solvent power of less than 5, and preferably less than 2. In some instances, the precipitant may have a solvent power of about 0. Suitable precipitants include alkanes, such as $C_{4-20}$ alkanes, and preferably $C_{4-20}$ n-alkanes or $C_{4-20}$ iso alkanes. In some instances, the precipitants are selected from heptane, undecane and pentadecane.

The reference oil and the precipitant may be equilibrated from 20 minutes to 40 minutes, such as 30 minutes. In some instances, the reference oil and the precipitant are undisturbed during this time, i.e. they are not subjected to any mixing or agitation. Titration intervals of less than 15% by volume, such as less than 10% by volume, and preferably less than 5% by volume may be used.

The hydrocarbon fluid and precipitant mixtures may be observed under an optical microscope to determine when asphaltene precipitation occurs. Alternatively, the mixtures may be subjected to centrifugation, with any solids washed (e.g. using the precipitant) and weighed to determine the amount of asphaltene precipitation.

Titration of the Light Oil Against the Reference Oil

Preferably, asphaltene precipitation is observed on titration of the light oil against the reference oil in the absence of a titrant. In these cases, x is 0 and the recalculated solvent power of the light oil, $SP_{(LO\ recalculated)}$, may be determined according to the following formula:

$$SP_{(LO\ recalculated)} = (CSP_{(RO)} - SP_{(RO)}) * V_{(onset\ fraction\ RO)} / V_{(onset\ fraction\ LO)}.$$

In these embodiments, the need to conduct experiments with artificial precipitants, such as n-heptane, is advantageously reduced.

However, in some cases, asphaltene precipitation may not be observed on titration of the light oil against solely the reference oil. In these cases, the light oil may be titrated against the reference oil in the presence of a titrant (i.e. x=1). This may be achieved e.g. by mixing the light oil with the titrant, and then combining varying amounts of reference oil and the mix; or by mixing the reference oil with the titrant, and then combining varying amounts of light oil and the mix. Preferably, the light oil is titrated against a mixture containing a reference oil and a titrant, where the reference oil and the titrant are present in the mixture in a ratio of from 2:1 to 1:2, and preferably from 1.5:1 to 1:1.5. In some instances, the reference oil and the titrant are present in the mixture in a ratio of about 1:1.

The titrant in these cases preferably has a negligible solvent power, such as a solvent power of less than 5, and preferably less than 2. In some instances, the precipitant may have a solvent power of about 0. Suitable titrants include alkanes, such as $C_{4-20}$ alkanes, and preferably $C_{4-20}$ n-alkanes or $C_{4-20}$ iso alkanes. In some instances, the titrants are selected from heptane, undecane and pentadecane. By using a titrant with negligible solvent power, asphaltene precipitation is encouraged, and the effect of the solvent power of the titrant on $SP_{(LO\ recalculated)}$ is minimal. Thus, the formula for determining the recalculated solvent power of the light oil, $SP_{(LO\ recalculated)}$, is as described in connection with embodiments in which a titrant is not used (i.e. x is 0). In contrast to embodiments in which a titrant is not used, the sum of $V_{(onset\ fraction\ RO)}$ and $V_{(onset\ fraction\ LO)}$ will be less than 1.

The titration of the light oil against the reference oil, optionally in the presence of a titrant, may be conducted with titration intervals of less than 15% by volume, such as less than 10% by volume, and preferably less than 5% by volume. A titration interval of 2% by volume is believed to give results which can be used to give a highly accurate estimate of the solvent power of a light oil.

The titration may comprise mixing the light oil with the reference oil. Mixing may be conducted using a sonicator or a vortex mixer.

The mixtures may be left to equilibrate for a period of at least 1 minute, such as from 3 minutes to 5 hours, and preferably from 5 minutes to 1 hour. Equilibration may take place at a temperature of from 0° C. to 100° C., such as from 10° C. to 80° C., and preferably from 20° C. to 60° C.

The mixtures may be observed, e.g. after equilibration, under an optical microscope to determine whether asphaltene precipitation has occurred. An optical microscope may be used at a magnification of 10× to 1000×, such as from 50× to 750×, and preferably from 100× to 500×. Gravimetric analysis of the blends, e.g. as disclosed in US 2004/0121472, may also be used.

In some cases, it may be desirable to conduct a first titration with large titration intervals and a second titration with small titration intervals. In this way, large titration intervals may be used to obtain a rough estimate of the volume fractions of the reference oil and the light oil at the onset of asphaltene precipitation, $V_{(onset\ fraction\ RO)}$ and $V_{(onset\ fraction\ LO)}$, and small titration intervals may then be used to determine an accurate measure of $V_{(onset\ fraction\ RO)}$ and $V_{(onset\ fraction\ LO)}$. The second titration need only be carried at intervals centered around the rough estimate of $V_{(onset\ fraction\ RO)}$ and $V_{(onset\ fraction\ LO)}$ that was obtained from the first titration, e.g. up to 25%, such as up to 15% by volume either side of the rough estimate of $V_{(onset\ fraction\ RO)}$ and $V_{(onset\ fraction\ LO)}$.

In some instances, the method of the present invention comprises titrating the light oil against a plurality of reference oils, predicting a solvent power of the light oil based on each of the plurality of reference oils, and determining an average predicted solvent power of the light oil.

By titrating the light oil against a plurality of reference oils, a plurality of predicted solvent powers may be obtained. These predicted solvent powers may then form the basis of an average predicted solvent power of the light oil.

The light oil may be titrated against at least 5, at least 10 or at least 20 reference oils. The greater the number of reference oils, the more accurate the average predicted solvent power of the light oil.

The average predicted solvent power of the light oil will generally be determined as a mean average predicted solvent power. However, it will be appreciated that other averages may be appropriate in some circumstances, e.g. to take account of outliers. Different methods for calculating averages are known in the art.

Determining the Relationship Between the Recalculated Solvent Powers and the Bulk Properties of a Light Oil In some instances, a plurality of light oils may be titrated against a reference oil so that the recalculated solvent power for each of the light oils may be determined. The recalculated solvent powers may then be correlated with the bulk properties of the light oils. This enables the recalculated solvent power of a light oil to be predicted merely from its bulk properties.

In some instances, at least 5 lights oil, such as at least 10 light oils, and preferably at least 20 light oils may be titrated against a reference oil.

It will be appreciated that the plurality of light oils may each be titrated against a single reference oil (the reference oil being the same or different for each of the oils of interest), or against a plurality of reference oils. By titrating each of the light oils against a plurality of reference oils, average recalculated solvent powers may be determined for each of the light oils.

In some instances, the method of predicting a relationship between the recalculated solvent powers and the bulk properties of a light oil may comprise the step of measuring the bulk properties of the plurality of light oils.

The skilled person would be aware of methods for determining a relationship between the recalculated solvent powers and the bulk properties of the plurality of light oils. Software is readily available for carrying out such methods.

Examples include the software program "Nutonian® Eureqa" (a registered trademark of Nutonian, Inc.), though other software packages may be used. In these instances, data on the bulk properties and the recalculated solvent powers of the light oils is used as an input, and the software generates a formula linking the recalculated solvent power to the bulk properties of the light oils. Multiple different formulae may be generated, in which case the operator may choose which of the formulae is most useful, e.g. includes bulk properties which are readily or reliably measurable.

Bulk properties may include: yield, e.g. of fractions of the light oil such as the vacuum gas oil (VGO) fraction; characterisation K factor, e.g. of the light oil; total acid number (TAN), e.g. of the light oil or fractions thereof; nitrogen content, e.g. of the light oil or fractions thereof; and API gravity, e.g. of the light oil or fractions thereof such as the VGO fraction; aromatics content, e.g. of the light oil or fractions thereof; and density, e.g. of the light oil or fractions thereof. Some or all of these properties may be taken into account when determining the relationship between the bulk properties of a light oil and its recalculated solvent power. Other bulk properties may also be used.

The yield of the different fractions, such as the VGO fraction, may be determined by distillation of the residue fraction (typically those components boiling above 300° C.) of the light oil according to ASTM D 5236. The residue is generated by distillation of the light oil according to ASTM D 2892. GC SIMDIS analysis (according to IP 545 and IP 507) of the residue fractions may be used to determine the yield of further fractions, including the VGO fraction.

The characterisation K factor may be calculated using the volume average boiling point and the density of the light oil, as discussed above in connection with the reference oil.

The nitrogen content of the light oil may be measured according to ASTM D 4629, IP 379 or equivalent.

TAN may be measured according to ASTM D 664 (IP 354) or ASTM D 974 (IP 139).

API gravity, e.g. of the VGO fraction, may be measured according to ASTM D 4052, ASTM D 5002, IP 365 or equivalents.

Aromatics content may be measured according to IP 548.

Density may be measured according to ASTM D 4052 or ASTM D 5002.

VGO is typically defined as material boiling in the range of from 350 to 580° C.

Though the bulk properties of the oils may by measured, e.g as outlined above, they are often readily available from oil assay analysis which has been carried out before the oil is purchased for use in a refinery. Moreover, in the absence of measured data, a crude oil property modelling tool such as CrudeSuite® (a registered trademark of Spiral Software Limited) may be used to predict properties using limited crude oil property measurements.

Once a relationship between the recalculated solvent powers and the bulk properties of the light oils has been determined, it may be used to predict the recalculated solvent power of a light oil from its bulk properties. The bulk properties of the light oil may be measured, or they may be readily available.

Reducing Asphaltene Precipitation in a Refinery

The recalculated solvent power of a light oil may be used in a method of reducing the precipitation of asphaltene from a blend of a light oil and a heavy oil in a refinery. Specifically, a maximum ratio of light oil that may be included in a blend of the light oil and the heavy oil without asphaltene precipitation occurring in the refinery may be calculated from the recalculated solvent power of the light oil. A blend of the light oil and the heavy oil having up to the maximum ratio of light oil may then be fed to the refinery.

The reduction in asphaltene precipitation may be observed in at least one of the tanks, pipes, heat exchangers, fired heater tubes, fractionators and reactors. Preferably, asphaltene precipitation is reduced on the surface of the heat exchangers in the refinery.

In some instances, the precipitation of asphaltene from the blend may be reduced by at least 80%, preferably at least 90%, and more preferably at least 95% by weight as compared to the precipitation that would be observed from the same weight of heavy oil.

The Light Oil and the Reference Oil

A light oil typically has an asphaltene content of less than 1% by weight, and preferably less than 0.5% by weight. A light oil may also have an API gravity of greater than 35°.

The reference oil is preferably a heavy oil. A heavy oil has an asphaltene content which is greater than that of the light oil, e.g. greater than 3% by weight, and preferably greater than 5% by weight. A heavy oil will typically also have an API gravity of less than 25°, and optionally a heavy residue content (i.e. components boiling above 1000° F., i.e. 537.8° C.) of greater than 30% by weight.

The asphaltene content of the oil of interest and the reference oil may be determined using known methods. For instance, the asphaltene content of each oil may be measured according to IP 143.

The API gravity of the light oil and the reference oil may be determined using known methods. For instance, the API gravity of each oil is preferably determined according to ASTM D 4052, though ASTM D 1298 may also be used.

The heavy residue content of the heavy oil may be determined using known methods. For instance, the heavy residue content of the oil may be determined according to ASTM D 5236 distillation of the residue (>300° C. boiling) produced from ASTM D 2892 distillation.

The light oil and the reference oil are preferably crude oils. Accordingly, they are preferably free from any asphaltene inhibitors and from any dispersants. The light oil and the reference oil are also preferably free from drilling mud, or any other contaminants.

EXAMPLES

Example 1: Recalculating the Solvent Power of a Light Crude Oil

Experiments for recalculating the solvent power of Oil A, a light crude oil, were carried out. Oil B, a heavy crude oil, was used as the reference oil.

Oil A was estimated, based on the characterisation K factor, to have a solvent power of 21 and a critical solvent power of 0. Oil A had a density at 15° C. of 0.7945 g/cm$^3$.

Oil B was estimated, based on the characterisation K factor, to have a solvent power of 37 and a critical solvent power of 24. Oil B had a density at 15° C. of 0.9136 g/cm$^3$.

According to the method disclosed in US 2004/0121472, Oil A could be blended with Oil B in an amount up to 80% by weight without asphaltene precipitation being observed.

To determine the recalculated solvent power, Oil A was titrated against Oil B in order to experimentally determine the point at which asphaltene precipitation was observed. Initial titration experiments were carried out using titration intervals of 10% by weight, with asphaltene precipitation measured using gravimetric analysis of the blends. It can be seen from FIG. 1 that minimum asphaltene precipitation was observed somewhere around 50% by weight of Oil. B.

A 'fine screen' titration was then carried out. Clean glass vials containing 5 g of Oil B were prepared. Varying masses of Oil A were added to the vials. The oils were mixed and equilibrated. Aliquots from the vials were viewed under an optical microscope (200×) to check for asphaltene precipitation. The results are shown in the following table:

| Vial | Amount of Oil B g | ml | Amount of Oil A g | ml | % by volume | Precipitation observed |
|---|---|---|---|---|---|---|
| 1 | 5.0018 | 5.47 | 4.2519 | 5.35 | 49.4 | No |
| 2 | 5.0012 | 5.47 | 4.5008 | 5.66 | 50.9 | No |
| 3 | 5.0021 | 5.48 | 4.7510 | 5.98 | 52.2 | Yes |
| 4 | 5.0018 | 5.47 | 5.0021 | 6.30 | 53.5 | Yes |
| 5 | 5.0005 | 5.47 | 5.2529 | 6.61 | 54.7 | Yes |

Figure 2A:
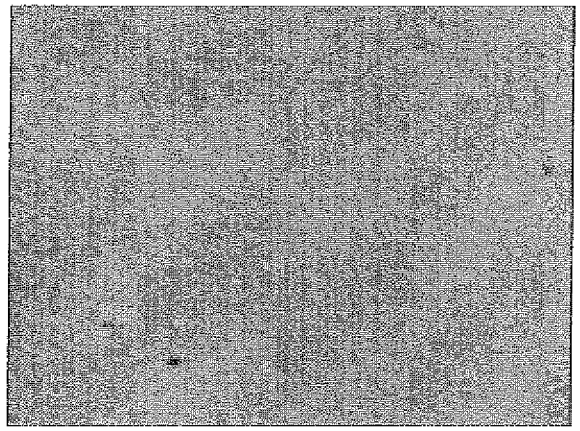
FIGS. 2a-c show optical microscope images of mixtures of Oils A and B.
Figure 2B:
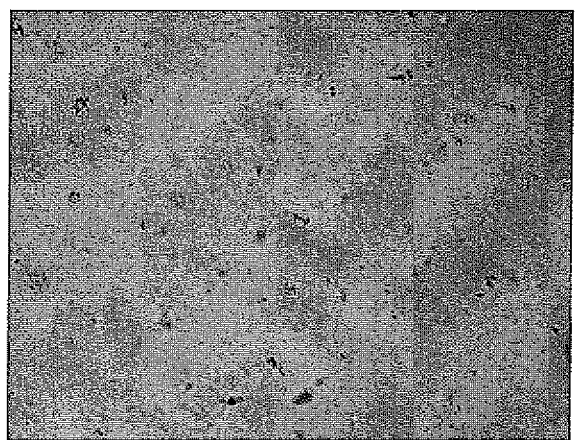
Figure 2C:
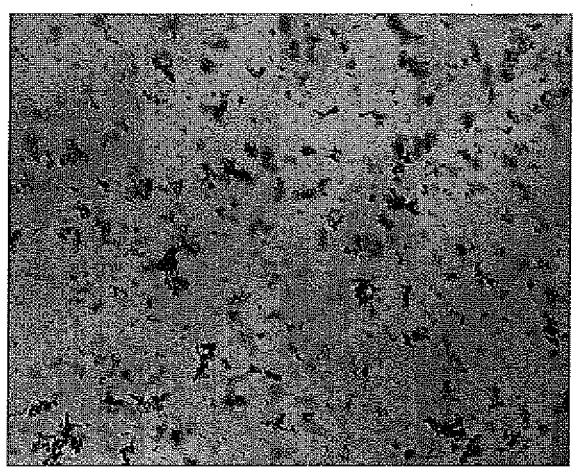

Optical microscopy images from vials 2-4 are shown in FIGS. 2a-c, respectively. It can be seen that negligible precipitation was observed in vial 2, with increasing levels of precipitation observed in vials 3 and 4 as the proportion of Oil A in the mixture increased.

The results indicate that the mixture of Oil A and Oil B was just stable at 50.9% by volume of Oil A.

The recalculated solvent power of Oil A was determined using Formula 1:

$$SP_{OilA(recalculated\ based\ on\ Oil\ B)} = (24 - 37*0.491)/0.509 = 11.46$$

This is significantly lower than predicted based on the characterisation K factor.

Example 2: Confirming the Recalculated Solvent Power of a Light Crude Oil

The recalculated solvent power of Oil A was confirmed by further experiments involving the titration of Oil A against different heavy oils, Oils C and D.

Oil C was estimated, based on the characterisation K factor, to have a solvent power of 36 and a critical solvent power of 18. Oil D was estimated, based on the characterisation K factor, to have a solvent power of 55 and a critical solvent power of 27.

Figure 3:
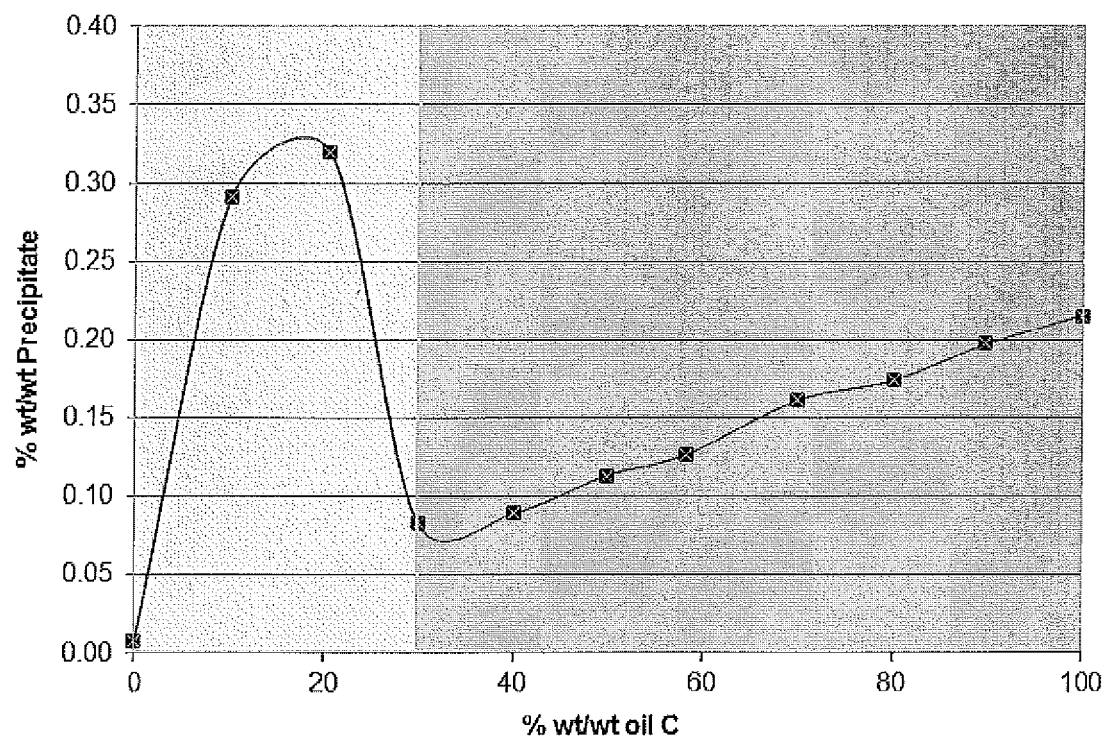
FIG. 3 is a graph showing the % by weight of precipitate that forms at different mixing ratios of a light crude oil, Oil A, with a heavy crude oil, Oil C.
Figure 4:
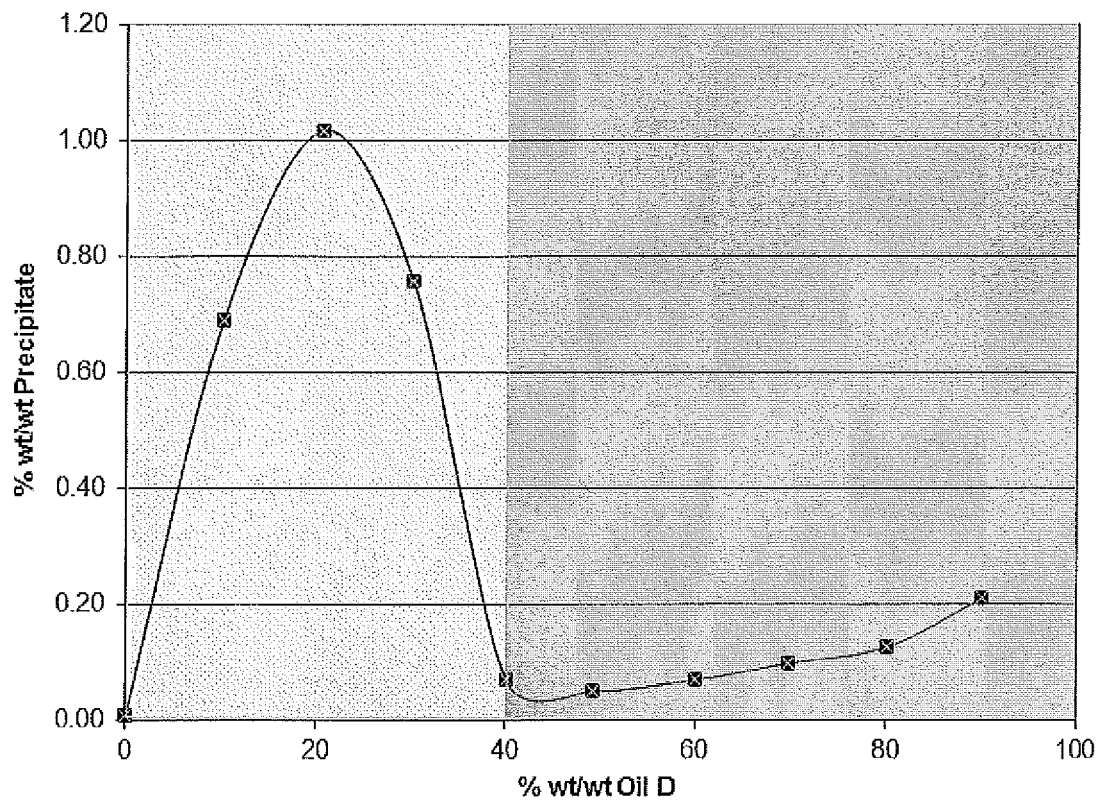
FIG. 4 is a graph showing the % by weight of precipitate that forms at different mixing ratios of a light crude oil, Oil A, with a heavy crude oil, Oil D.

Initial titration experiments were carried out using titration intervals of 10% by weight, with asphaltene precipitation measured using gravimetric analysis of the blends. It can be seen from FIG. 3 that minimum asphaltene precipitation was observed somewhere around 30% by weight of Oil C, and from FIG. 4 that minimum asphaltene precipitation was observed somewhere around 50% by weight of Oil D.

'Fine screen' titrations were then carried out. Oil A was blended with Oil C in an amount of up to 74% by volume and with Oil D in an amount of up to 65% by volume before asphaltene precipitation was observed.

The recalculated solvent power of Oil A was determined using Formula 1:

$$SP_{OilA(recalculated\ based\ on\ Oil\ C)} = (18 - 36*0.26)/0.74 = 11.68$$

$$SP_{OilA(recalculated\ based\ on\ Oil\ D)} = (27 - 55*0.35)/0.65 = 11.92$$

It can be seen that the recalculated solvent power of Oil A based on Oils C and D is aligned with that based on Oil B, demonstrating that the method of the present invention gives consistent results when different reference oils are used.

Example 3: Determining a Relationship Between Recalculated Solvent Power and Bulk Properties of Light Crude Oils Experiments were conducted for a large range of light oils in order to determine a relationship between the recalculated solvent power and the bulk properties of light crude oils.

More than 200 light crude oils were titrated against a heavy reference oil, or a heavy reference oil and a n-heptane titrant, to determine their recalculated solvent power. The titrations were carried out using titration intervals of 2% by weight. The onset of asphaltene precipitation was monitored using microscopy.

Standard experiments were also carried out to determine the bulk properties of the light crude oils.

The data from approximately 150 of the light crude oils was investigated for correlations between the recalculated solvent powers and bulk properties of the oils using the software program "Nutonian Eureqa". The following relationship was determined:

$$\text{Solvent power} = 0.50 * \text{yield of vacuum gas oil (vol \%)} +$$
$$2.6*10^{-3} * \text{characterisation } K \text{ factor} * \text{total nitrogen content (ppm)} +$$
$$0.77 * [\text{total acid number (mg KOH/g)}]^2 -$$
$$0.024 * \text{total nitrogen content (ppm)} - 22.9 * \text{characterisation } K \text{ factor} -$$
$$0.018 * \text{yield of vacuum gas oil (vol \%)} * API \text{ of vacuum gas oil} -$$
$$7.18*10^{-7} * [\text{total nitrogen content (ppm)}]^2 + 288.7$$

Example 4: Predicting the Recalculated Solvent Power of a Light Crude Oil

The formula determined in Example 3 was used to predict the recalculated solvent power of 200 light crude oils. Approximately 150 of these oils were already used in the development of the formula, as described above, with datasets from the remaining oils also being used to test the accuracy of the formula.

Figure 5:
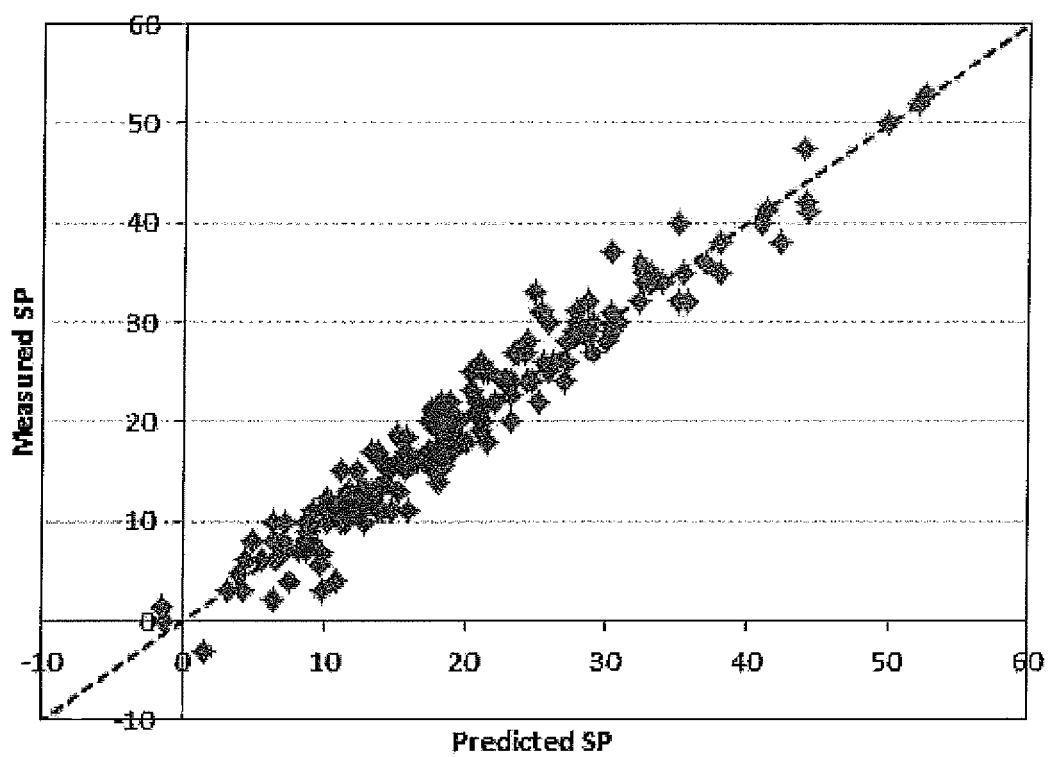
FIG. 5 is a graph comparing the predicted recalculated solvent power and the recalculated solvent power as determined using titrations in accordance with the method of the present invention for 150 light crude oils.

The recalculated solvent power as predicted using the formula determined in Example 3 was compared with the recalculated solvent power as determined using titrations in accordance with the method of the present invention. The data is shown as a graph in FIG. 5. A mean error of 0.17 solvent power units is associated with the predicted recalculated solvent power, thereby demonstrating the accuracy of the methods disclosed herein.

The invention claimed is:

1. A method of preparing a blend of a light oil and a heavy oil in a refinery, the blend having a reduced degree of precipitation of asphaltene, said method comprising:

titrating the light oil against a reference oil, optionally in the presence of a titrant, to determine a volume fraction of the light oil at the onset of asphaltene precipitation, $V_{(onset\ fraction\ LO)}$, a volume fraction of the reference oil at the onset of asphaltene precipitation, $V_{(onset\ fraction\ RO)}$, and, where a titrant is present, a volume fraction of the titrant at the onset of asphaltene precipitation, $V_{(onset\ fraction\ T)}$, determining the recalculated solvent power of the light oil, $SP_{(LO\ recalculated)}$, using the following formula:

$$SP_{(LO\ recalculated)} = \frac{\left(\begin{array}{c} CSP_{(RO)} - SP_{(RO)} * V_{(onset\ fraction\ RO)} - \\ x * SP_{(T)} * V_{(onset\ fraction\ T)} \end{array}\right)}{V_{(onset\ fraction\ LO)}}$$

wherein:
  $CSP_{(RO)}$ is the critical solvent power of the reference oil,
  $SP_{(RO)}$ is the solvent power of the reference oil,
  $SP_{(T)}$ is the solvent power of the titrant, and
  x is 1 where a titrant is present, and otherwise is 0;
calculating, based on the recalculated solvent power of the light oil, a maximum ratio of light oil that may be included in a blend of the light oil and the heavy oil without asphaltene precipitation occurring in the refinery; and
feeding a blend of the light oil and the heavy oil having up to the maximum ratio of light oil to the refinery.

2. The method of claim 1, wherein the precipitation of asphaltene from the blend may be reduced by at least 80% by weight as compared to the precipitation that would be observed from the same weight of heavy oil.

3. The method of claim 1, wherein the precipitation of asphaltene is reduced on the surface of heat exchangers in the refinery.

4. The method of claim 1, wherein titration intervals of less than 15% by weight are used for titrating the light oil against the reference oil.

5. The method of claim 1, wherein the light oil is titrated against the reference oil in the presence of a titrant and x is 1.

6. The method of claim 1, wherein the method comprises titrating the light oil against a plurality of reference oils, predicting a solvent power of the light oil for each of the plurality of reference oils and determining an average predicted solvent power of the light oil.

7. The method of claim 6, wherein the light oil is titrated against at least 5 reference oils.

8. The method of claim 1, wherein the solvent power of the reference oil, $SP_{(RO)}$, is estimated from the characterisation K factor of the reference oil.

9. The method of claim 1, wherein the critical solvent power of the reference oil, $CSP_{(RO)}$, is determined by titrating the reference oil against a precipitant.

10. The method of claim 1, wherein the light oil has an asphaltene content of less than 1% by weight.

11. The method of claim 1, wherein the reference oil has an asphaltene content of greater than 3% by weight.

12. The method of claim 1, wherein the light oil and the reference oil are crude oils.

13. The method of claim 1 further comprising determining a relationship between the recalculated solvent power and the bulk properties of the plurality of light oils.

14. The method of claim 13, wherein the method comprises measuring the bulk properties of the plurality of light oils.

15. The method of claim 13, wherein the plurality of light oils consists of at least 5 light oils.

16. The method of claim 13, wherein the bulk properties include at least one of: yield, characterization K factor, total acid number (TAN), nitrogen content, API gravity, aromatics content, and density.

17. The method of claim 13, further comprising using the relationship between the recalculated solvent power and the bulk properties of the plurality of light oils to predict the recalculated solvent power of a light oil from its bulk properties.

18. The method of claim 17, further comprising measuring the bulk properties of the light oil.

* * * * *